US012765849B2

(12) United States Patent
Tsukagoshi et al.

(10) Patent No.: US 12,765,849 B2
(45) Date of Patent: Oct. 20, 2026

(54) MEDICAL IMAGE PROCESSING DEVICE AND MEDICAL IMAGE PROCESSING METHOD

(71) Applicant: Canon Kabushiki Kaisha, Tokyo (JP)

(72) Inventors: Shinsuke Tsukagoshi, Nasushiobara (JP); Hiroki Taguchi, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 377 days.

(21) Appl. No.: 18/475,617

(22) Filed: Sep. 27, 2023

(65) Prior Publication Data

US 2024/0099675 A1 Mar. 28, 2024

(30) Foreign Application Priority Data

Sep. 28, 2022 (JP) ................................ 2022-154796

(51) Int. Cl.
*A61B 6/42* (2024.01)
*G06T 12/00* (2026.01)

(52) U.S. Cl.
CPC ............ *A61B 6/4241* (2013.01); *G06T 12/00* (2026.01); *G06T 2207/10081* (2013.01)

(58) Field of Classification Search
CPC ....... A61B 6/4241; A61B 6/469; A61B 6/032; A61B 6/482; A61B 6/5205; G06T 11/003; G06T 2207/10081
See application file for complete search history.

(56) References Cited

U.S. PATENT DOCUMENTS 9,836,859 B2 * 12/2017 Zou ...................... A61B 6/4241
2007/0076842 A1 * 4/2007 Tkaczyk ............. A61B 6/4085 378/108

(Continued)

FOREIGN PATENT DOCUMENTS

JP 2015-136461 A 7/2015
JP 2018-42604 A 3/2018

OTHER PUBLICATIONS

Lee, CL., Hong, K.J., Kim, N. et al. Feasibility study of portable multi-energy computed tomography with photon-counting detector for preclinical and clinical applications. Sci Rep 11, 22731 (2021). https://doi.org/10.1038/s41598-021-02210-5 (Year: 2021).*

(Continued)

*Primary Examiner* — Chan S Park
*Assistant Examiner* — Chandhana Pedapati
(74) *Attorney, Agent, or Firm* — Oblon, McClelland, Maier & Neustadt, L.L.P.

(57) ABSTRACT

A medical image processing device includes processing circuitry. The processing circuitry sets a first energy bin at a k-absorption edge of a specific substance and sets a second energy bin and a third energy bin on both sides of the first energy bin. The processing circuitry generates a first medical image and a second medical image in which the specific substance is more emphasized using data of the energy bins. The processing circuitry outputs the medical images via an output interface. The processing circuitry sets a weighting for the data in the first energy bin when the second medical image is generated to be less than a weighting for the data in the second energy bin when the second medical image is generated and to be less than a weighting for the data in the first energy bin when the first medical image is generated.

16 Claims, 7 Drawing Sheets

(56) References Cited

U.S. PATENT DOCUMENTS

| | | | | |
|---|---|---|---|---|
| 2011/0129132 | A1* | 6/2011 | Tsukerman | A61B 5/055 382/128 |
| 2014/0105364 | A1* | 4/2014 | Han | G01N 23/087 378/91 |
| 2014/0254757 | A1* | 9/2014 | Oh | G01T 1/247 378/62 |
| 2014/0355853 | A1* | 12/2014 | Zou | A61B 6/5258 382/131 |
| 2015/0257722 | A1* | 9/2015 | Wang | A61B 6/032 250/336.1 |
| 2015/0287193 | A1* | 10/2015 | Kato | A61B 6/482 382/131 |
| 2016/0242727 | A1* | 8/2016 | Flohr | A61B 6/032 |
| 2020/0234471 | A1* | 7/2020 | Lu | G06T 11/005 |
| 2020/0323502 | A1 | 10/2020 | Kojima et al. | |
| 2021/0022695 | A1* | 1/2021 | Iniewski | A61B 6/58 |
| 2022/0028127 | A1* | 1/2022 | Daerr | A61B 6/032 |
| 2025/0327939 | A1* | 10/2025 | Solf | G01T 1/17 |

OTHER PUBLICATIONS

Kalluri KS, Mahd M, Glick SJ. Investigation of energy weighting using an energy discriminating photon counting detector for breast CT. Med Phys. Aug. 2013;40(8):081923. doi: 10.1118/1.4813901. PMID: 23927337; PMCID: PMC3745502. (Year: 2013).*

Schmidt, Taly Gilat, "Optimal "Image-Based" Weighting for Energy-Resolved CT" (2009). Biomedical Engineering Faculty Research and Publications. 74. https://epublications.marquette.edu/bioengin_fac/74 (Year: 2009).*

Ms. Yirong Yang, Dr. Sen Wang, Dr. Debashish Pal, et al. "Empirical optimization of energy bin weights for compressing measurements with photon counting x-ray detectors", Proc. SPIE 12031, Medical Imaging 2022: Physics of Medical Imaging, 120310E (Apr. 4, 2022); https://doi.org/10.1117/12.2611555 (Year: 2022).*

* cited by examiner

MEDICAL IMAGE PROCESSING DEVICE AND MEDICAL IMAGE PROCESSING METHOD

CROSS-REFERENCE TO RELATED APPLICATION

The present application claims priority based on Japanese Patent Application No. 2022-154796 filed on Sep. 28, 2022, the content of which is incorporated herein by reference.

FIELD

Embodiments disclosed in the present specification and the drawings relate to a medical image processing device and a medical image processing method.

BACKGROUND

A photon counting computed tomography (CT) scanner is a diagnostic imaging device that can discriminate a detection target substance (a specific substance) having transmitted X-rays using a direct detector such as a semiconductor detector with desirable energy resolution. The photon counting CT scanner counts X-ray photons for each of energy bands (hereinafter referred to as an "energy bin") and generates a CT image on the basis of the counted X-ray photons.

When the photon counting CT scanner is used for clinical use, the energy of a k-edge (k-absorption edge) of a specific substance to be detected may spread when it is detected due to various physical phenomena (such as scattered radiation) and hence the steep edges are blurred. As a result, a medical image in which the specific substance is emphasized may not be acquired, or the quality of the medical image may decrease.

DETAILED DESCRIPTION

Hereinafter, a medical image processing device and a medical image processing method according to an embodiment will be described with reference to the accompanying drawings. A medical image processing device according to an embodiment includes processing circuitry. The processing circuitry sets a first energy bin in a first energy range including energy of a k-absorption edge of a specific substance, sets a second energy bin in a second energy range with higher energy than the first energy range, and sets a third energy bin in a third energy range with lower energy than the first energy range.

The processing circuitry generates a first medical image and a second medical image in which the specific substance is more emphasized in comparison with the first medical image using data based on X-ray photons counted in each of the first energy bin, the second energy bin, and the third energy bin. The processing circuitry outputs the first medical image and the second medical image via an output interface.

The processing circuitry sets a weighting for the data in the first energy bin when the second medical image is generated to be less than a weighting for the data in the second energy bin when the second medical image is generated and to be less than a weighting for the data in the first energy bin when the first medical image is generated. Accordingly, it is possible to generate a medical image with higher quality.

[Configuration of X-Ray CT Scanner]

Figure 1:
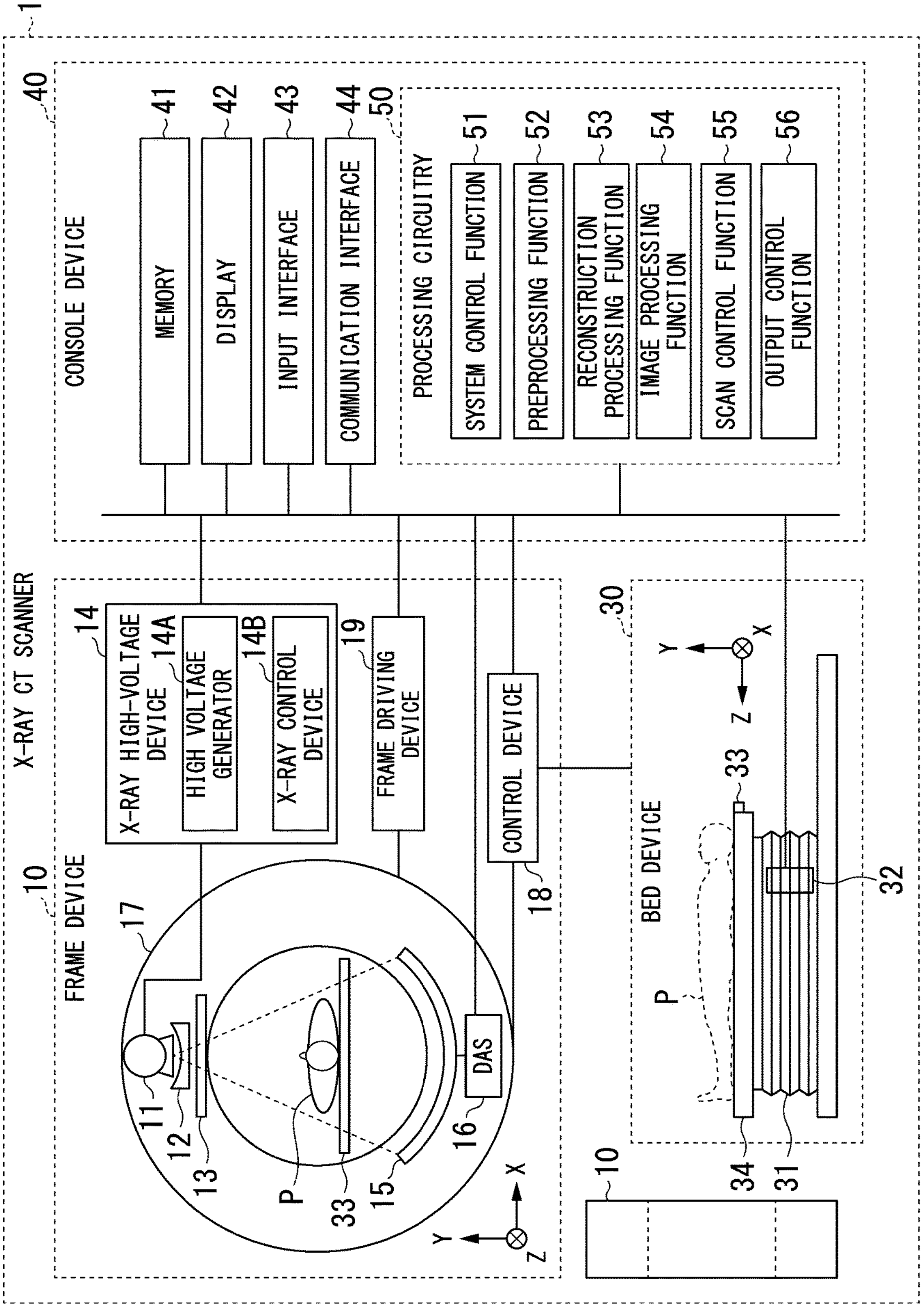
FIG. 1 is a diagram illustrating an example of a configuration of an X-ray CT scanner according to an embodiment.

FIG. 1 is a diagram illustrating an example of a configuration of an X-ray CT scanner 1 according to the embodiment. The X-ray CT scanner according to the embodiment is a photon counting CT scanner. The photon counting CT scanner discriminates a specific substance transmitting X-rays using a direct detector. The X-ray CT scanner 1 includes, for example, a frame device 10, a bed device 30, and a console device 40. In FIG. 1, both a view of the frame device 10 when seen in a Z-axis direction and a view of the frame device 10 when seen in an X-axis direction are illustrated for the purpose of convenience of explanation, but the actual number of frame devices 10 is one. In this embodiment, a rotation shaft of a rotary frame 17 in a non-tilted state or a longitudinal direction of a top plate 33 of the bed device 30 is defined as a Z-axis direction, a direction perpendicular to the Z-axis direction and parallel to the floor is defined as an X-axis direction, and a direction perpendicular to the Z-axis direction and perpendicular to the floor is defined as a Y-axis direction.

The frame device 10 includes, for example, an X-ray tube 11, a wedge 12, a collimator 13, an X-ray high-voltage device 14, an X-ray detector 15, a data acquisition system (hereinafter referred to as a DAS) 16, a rotary frame 17, a control device 18, and a frame driving device 19. The rotary frame 17 holds the X-ray tube 11 and the X-ray detector 15 such that they are rotatable.

The X-ray tube 11 generates X-rays by radiating thermoelectrons from a cathode (a filament) to an anode (a target) with application of a high voltage from the X-ray high-voltage device 14. The X-ray tube 11 includes a vacuum tube. For example, the X-ray tube 11 is a rotary anode type X-ray tube that generates X-rays by radiating thermoelectrons to the rotating anode.

The wedge 12 is a filter for adjusting an X-ray dose radiated from the X-ray tube 11 to an examinee P. The wedge 12 attenuates X-rays transmitted by the wedge such that a distribution of an X-ray dose radiated from the X-ray tube 11 to the examinee P becomes a predetermined distribution. The wedge 12 is also referred to as a wedge filter or bow-tie filter. The wedge 12 is formed, for example, by processing aluminum to have a predetermined target angle or a predetermined thickness.

The collimator 13 is a mechanism for narrowing an irradiation range with X-rays transmitted by the wedge 12. The collimator 13 narrows the irradiation range with X-rays, for example, by forming a slit by combining a plurality of lead plates. The collimator 13 may be referred to as an X-ray iris diaphragm. The narrowing range of the collimator 13 may be mechanically driven.

The X-ray high-voltage device 14 includes, for example, a high voltage generator 14A and an X-ray control device 14B. The high voltage generator 14A includes an electrical circuit including a voltage transformer and a current rectifier and generates a high voltage which is applied to the X-ray tube 11. The high voltage generator 14A may perform step-up using the voltage transformer or may perform step-up using an inverter.

The X-ray control device 14B includes, for example, processing circuitry including a processor such as a central processing unit (CPU). The X-ray control device 14B receives an input signal from an input interface 43 attached to the console device 40 or the frame device 10 and controls operations of the collimator 13 and the high voltage generator 14A. The X-ray control device 14B adjusts the irradiation range with X-rays by controlling the collimator 13. The X-ray control device 14B controls an output voltage of the high voltage generator 14A, for example, on the basis of an X-ray dose to be generated by the X-ray tube 11. The X-ray high-voltage device 14 may be provided in the rotary frame 17 or may be provided in a fixed frame (not illustrated) of the frame device 10.

The X-ray detector 15 detects an intensity of X-rays which are generated by the X-ray tube 11, pass through an examinee P, and are incident thereon. The X-ray detector 15 outputs an electrical signal (which may be an optical signal) corresponding to the detected intensity of X-rays to the DAS 16. The X-ray detector 15 includes, for example, a plurality of X-ray detection element lines. In each of the plurality of X-ray detection element lines, a plurality of X-ray detection elements are arranged in a channel direction along an arc centered on the focal point of the X-ray tube 11. The plurality of X-ray detection element lines is arranged in slice directions (a column direction, a row direction).

The X-ray detector 15 is, for example, a direct detection type detector. For example, a semiconductor diode in which electrodes are attached to both ends of a semiconductor can be used as the X-ray detector 15. X-ray photons incident on the semiconductor are converted to electron-hole pairs. The number of electron-hole pairs which are generated in response to incidence of one X-ray photon depends on the energy of the incident X-ray photon. Electrons and holes are attracted to a pair of electrodes formed at both ends of the semiconductor. The pair of electrodes generates electrical pulses having a peak value corresponding to the electric charge of the electron-hole pairs. One electrical pulse has a peak value corresponding to the energy of the incident X-ray photons.

For example, the DAS 16 acquires count data indicating a counted number (a counted value) of X-ray photons detected by the X-ray detector 15 for each energy bin in accordance with a control signal from the control device 18. The count data for each energy bin corresponds to the energy spectrum for X-rays incident on the X-ray detector 15 and deformed according to response characteristics of the X-ray detector 15. The DAS 16 outputs count data based on a digital signal as detection data to the console device 40. The detection data includes a digital value of the count data identified by a channel number and a line number of the X-ray detection element which is a source and a view number indicating a collected view. The view number is a number changing with rotation of the rotary frame 17 and is, for example, a number increasing with rotation of the rotary frame 17. Accordingly, the view number is information indicating a rotational angle of the X-ray tube 11. A view period is a period required for the rotary frame 17 to rotate from a rotational angle corresponding to a certain view number to a rotational angle corresponding to a next view number. The DAS 16 may detect switching a view on the basis of a timing signal input from the control device 18, using an internal timer, or on the basis of a signal acquired from a sensor which is not illustrated. When X-rays are continuously radiated by the X-ray tube 11 in full scanning, the DAS 16 collects a detection data group corresponding to a full circumference (360 degrees). When X-rays are continuously radiated by the X-ray tube 11 in half scanning, the DAS 16 collects detection data corresponding to a half circumference (180 degrees).

Figure 2:
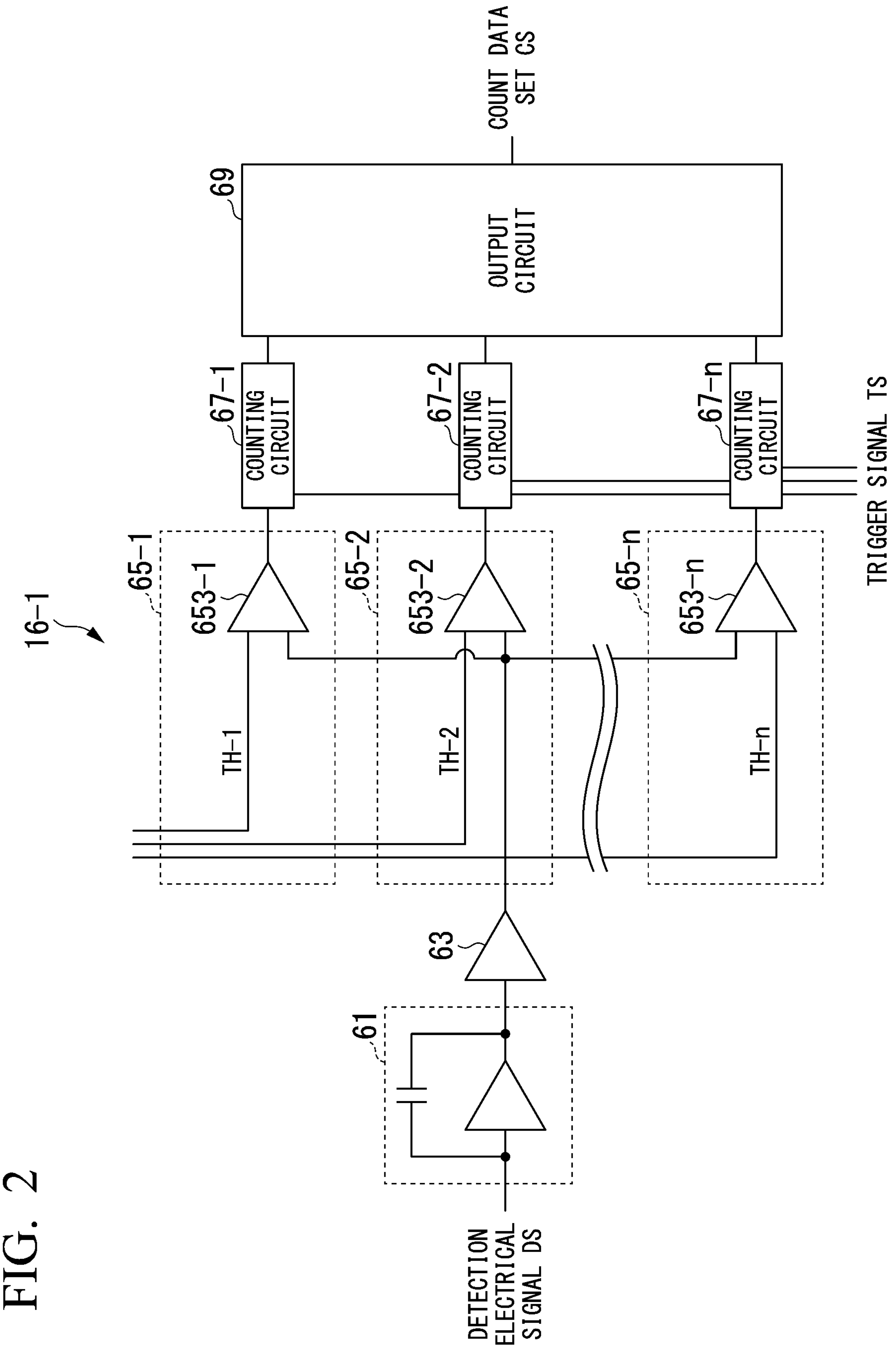
FIG. 2 is a diagram illustrating an example of a configuration of a DAS according to the embodiment.

FIG. 2 is a diagram illustrating an example of a configuration of the DAS 16 according to the embodiment. The DAS 16 includes reading channels corresponding to the number of channels based on the number of X-ray detection elements. The plurality of reading channels is mounted in parallel in an integrated circuit such as an application-specific integrated circuit (ASIC). In FIG. 2, only the configuration of the DAS 16-1 corresponding to one reading channel is illustrated.

The DAS 16-1 includes a preamplifier circuit 61, a waveform shaping circuit 63, a plurality of peak discriminating circuits 65, a plurality of counting circuits 67, and an output circuit 69. The preamplifier circuit 61 amplifies a detection electrical signal DS (a current signal) from an X-ray detection element which is a connection destination. For example, the preamplifier circuit 61 converts the current signal from the X-ray detection element which is a connection destination to a voltage signal having a voltage value (a peak value) proportional to an amount of electric charge of the current signal. The waveform shaping circuit 63 is connected to the preamplifier circuit 61. The waveform shaping circuit 63 shapes the waveform of the voltage signal from the preamplifier circuit 61. For example, the waveform shaping circuit 63 decreases the pulse width of the voltage signal from the preamplifier circuit 61.

A plurality of counting channels corresponding to the number of energy bands (energy bins) is connected to the waveform shaping circuit 63. When n energy bins are set, n counting channels are provided in the waveform shaping circuit 63. Each counting channel includes a peak discriminating circuit 65-*n* and a counting circuit 67-*n*.

Each peak discriminating circuit 65-*n* discriminates energies of X-ray photons which are detected by the X-ray detection element and which is a peak value of a voltage signal from the waveform shaping circuit 63. For example, the peak discriminating circuit 65-*n* includes a comparison circuit 653-*n*. A voltage signal from the waveform shaping circuit 63 is input to one input terminal of each comparison circuit 653-*n*. A reference signal TH (a reference voltage value) corresponding to another threshold value is supplied to the other input terminal of the comparison circuit 653-*n* from the control device 18. For example, a reference signal TH-1 is supplied to the comparison circuit 653-1 for an energy bin bin1, a reference signal TH-2 is supplied to the comparison circuit 653-2 for an energy bin bin2, and a reference signal TH-n is supplied to the comparison circuit 653-*n* for an energy bin binn. Each reference signal TH includes an upper-limit reference value and a lower-limit reference value. When the voltage signal from the waveform shaping circuit 63 has a peak value corresponding to the energy bin corresponding to the reference signal TH, each comparison circuit 653-*n* outputs an electrical pulse signal. For example, when the peak value of the voltage signal from the waveform shaping circuit 63 is a peak value corresponding to the energy bin bin1 (when the peak value is between the reference signal TH-1 and the reference signal TH-2), the comparison circuit 653-1 outputs an electrical pulse signal. On the other hand, when the peak value of the voltage signal from the waveform shaping circuit 63 is not a peak value corresponding to the energy bin bin1, the comparison circuit 653-1 for the energy bin bin1 does not output an electrical pulse signal. For example, when the peak value of the voltage signal from the waveform shaping circuit 63 is a peak value corresponding to the energy bin bin2 (when the peak value is between the reference signal TH-2 and the reference signal TH-3), the comparison circuit 653-2 outputs an electric pulse signal.

The counting circuit 67-*n* counts the electrical pulse signal from the peak discriminating circuit 65-*n* in a reading cycle corresponding to a view switching period. For example, the counting circuit 67-*n* is supplied with a trigger signal TS from the control device 18 at each view switching timing. With supply of the trigger signal TS as a trigger, the counting circuit 67-*n* adds 1 to the count number stored in an internal memory whenever an electrical pulse signal is input from the peak discriminating circuit 65-*n*. With next supply of the trigger signal TS as a trigger, the counting circuit 67-*n* reads data of the count number (that is, count data) stored in the internal memory and supplies the count data to the output circuit 69. The counting circuit 67-*n* resets the count number stored in the internal memory to an initial value whenever the trigger signal TS is supplied. In this way, the counting circuit 67-*n* counts the count number for each view.

The output circuit 69 is connected to the counting circuits 67-*n* corresponding to the plurality of reading channels mounted in the X-ray detector 15. The output circuit 69 collects count data from the counting circuits 67-*n* corresponding to the plurality of reading channels for each of the plurality of energy bins and generates count data corresponding to the plurality of reading channels for each view. The count data for each energy bin is a set of data of the count number defined by the channels, the segments (lines), and the energy bin. The count data for each energy bin is transmitted to the console device 40 for each view. The count data for each view is referred to as a count data set CS.

The rotary frame 17 is an arc-shaped member supporting the X-ray tube 11, the wedge 12, and the collimator 13 and the X-ray detector 15 such that they face each other. The rotary frame 17 is supported to be rotatable about an examinee P introduced thereinto by a fixed frame. The rotary frame 17 additionally supports the DAS 16. Detection data output from the DAS 16 is transmitted from a transmitter including a light emitting diode (LED) provided in the rotary frame 17 to a receiver including a photo diode provided in a non-rotary part (for example, a fixed frame) of the frame device 10 by optical communication and is then transmitted to the console device 40 by the receiver. The method of transmitting detection data from the rotary frame 17 to the non-rotary part is not limited to the method using optical communication, and a non-contact arbitrary transmission method may be employed. The rotary frame 17 is not limited to the arc-shaped member as long as it can support and rotate the X-ray tube 11 and the like and may be an arm-like member.

The X-ray CT scanner 1 is, for example, a rotate/rotate-type X-ray CT scanner (a third-generation CT) in which both the X-ray tube 11 and the X-ray detector 15 are supported by the rotary frame 17 and rotate around an examinee P, but it is not limited thereto and may be a stationary/rotate-type X-ray CT scanner (a fourth-generation CT) in which a plurality of X-ray detection elements arranged in an arc shape are fixed to a fixed frame and the X-ray tube 11 rotates around an examinee P.

The control device 18 includes, for example, processing circuitry including a processor such as a central processing unit (CPU). The control device 18 receives an input signal from an input interface 43 attached to the console device 40 or the frame device 10 and controls operations of the frame device 10, the bed device 30, and the DAS 16. For example, the control device 18 controls the frame driving device 19 such that the rotary frame 17 is rotated or the frame device 10 is tilted. When the frame device 10 is tilted, the control device 18 controls the frame driving device 19 on the basis of a tilt angle input to the input interface 43 such that the rotary frame 17 is rotated about an axis parallel to the Z-axis direction. The control device 18 ascertains a rotation angle of the rotary frame 17 on the basis of an output of a sensor which is not illustrated or the like. The control device 18 frequently sends the rotation angle of the rotary frame 17 to a scanning control function 55 or the like. The control device 18 controls an energy bin (a reference signal TH) of the DAS 16. The control device 18 may be provided in the frame device 10 or may be provided in the console device 40.

The frame driving device 19 includes, for example, a motor or an actuator. For example, the frame driving device 19 rotates the rotary frame 17 or tilts the frame device 10. The frame driving device 19 rotates the rotary frame 17 of the frame device 10 on the basis of a tilt angle input to the input interface 43 or a rotation instruction from the processing circuitry 50.

The bed device 30 is a device which allows an examinee P which is a scanning target to be placed thereon and to move and which introduces the examinee P into the rotary frame 17 of the frame device 10. The bed device 30 includes, for example, a base 31, a bed driving device 32, a top plate 33, and a support frame 34. The base 31 includes a casing that supports the support frame 34 to be movable in the vertical direction (the Y-axis direction). The bed driving device 32 includes a motor or an actuator. The bed driving device 32 moves the top plate 33 in the longitudinal direction (the Z-axis direction) of the top plate 33 along the support frame 34. The bed driving device 32 moves the top plate 33 in the vertical direction (the Y-axis direction). The top plate 33 is a plate-shaped member on which an examinee P is placed.

The bed driving device 32 may move the support frame 34 in addition to the top plate 33 in the longitudinal direction of the top plate 33. On the other hand, the frame device 10 may be movable in the Z-axis direction, and control may be performed such that the rotary frame 17 approaches an examinee P with movement of the frame device 10. Both the frame device 10 and the top plate 33 may be configured to be movable. The X-ray CT scanner 1 may be a device of a type in which an examinee P is scanned in an upright position or a sitting position. In this case, the X-ray CT scanner 1 includes an examinee support mechanism instead of the bed device 30, and the frame device 10 rotates the rotary frame 17 about an axis direction perpendicular to the floor.

The console device 40 includes, for example, a memory 41, a display 42, an input interface 43, a communication interface 44, and processing circuitry 50. In this embodiment, the console device 40 is provided separate from the frame device 10, but some or all of constituents of the console device 40 may be included in the frame device 10.

The memory 41 is realized, for example, by a semiconductor memory device such as a random access memory (RAM) or a flash memory, a hard disk, and an optical disc. The memory 41 stores, for example, detection data, projection data, CT images, information on an examinee P, and imaging conditions. The memory 41 stores, for example, count data of a plurality of energy bins transmitted from the frame device 10. Such data may be stored in an external memory that can communicate with the X-ray CT scanner 1 instead of the memory 41 (or in addition to the memory 41). The external memory is controlled, for example, by a cloud server managing the external memory by causing the cloud server to receive a reading/writing request.

The display 42 displays various types of information. For example, the display 42 displays a medical image (a CT image) generated by the processing circuitry or a graphical user interface (GUI) image for receiving various operations from an operator such as a doctor or an engineer. The display 42 is, for example, a liquid crystal display, a cathode ray tube (CRT), or an organic electroluminescence (EL) display. The display 42 may be provided in the frame device 10. The display 42 may be a desktop or may be a display device (for example, a tablet terminal) that can wirelessly communicate with a main body part of the console device 40. The display 42 is an example of an "output interface."

The input interface 43 receives various input operations from an operator and outputs an electrical signal indicating details of the received input operation to the processing circuitry 50. For example, the input interface 43 receives an input operation of collection conditions for collecting detection data or projection data (which will be described later), reconstruction conditions for reconstructing a CT image, and image processing conditions for generating a post-processed image from the CT image.

For example, the input interface 43 may be realized by a mouse, a keyboard, a touch panel, a trackball, switches, buttons, a joystick, a camera, an infrared sensor, or a microphone. The input interface 43 may be provided in the frame device 10. The input interface 43 may be realized by a display device (for example, a tablet terminal) that can wirelessly communicate with the main body part of the console device 40. The input interface in this specification is not limited to an input interface including physical operation components such as a mouse and a keyboard. For example, the input interface may include processing circuitry that receives an electrical signal corresponding to an input operation from an external input device provided separately from the device and outputs the electrical signal to a control circuit.

The communication interface 44 includes, for example, a network card including a printed circuit board or a wireless communication module. The communication interface 44 has an information communication protocol corresponding to a network type to be connected thereto. The communication interface 44 is another example of an "output interface."

The processing circuitry 50 controls the whole operations of the X-ray CT scanner 1, the operation of the frame device 10, and the operation of the bed device 30. The processing circuitry 50 performs, for example, a system control function 51, a preprocessing function 52, a reconstruction function 53, an image processing function 54, a scanning control function 55, and an output control function 56. The system control function 51 is an example of a "setting unit." A combination of the preprocessing function 52, the reconstruction function 53, and the image processing function 54 is an example of a "generation unit." The output control function 56 is an example of an "output control unit."

These constituent elements are realized, for example, by causing a hardware processor (a computer) to execute a program (software) stored in the memory 41. The hardware processor means, for example, circuitry such as a CPU, a graphics processing unit (GPU), an application-specific integrated circuit (ASIC), a programmable logic device (for example, a simple programmable logic device (SPLD) or a complex programmable logic device (CPLD)), or a field-programmable gate array (FPGA). Instead of storing the program in the memory 41, the program may be directly assembled into circuitry of the hardware processor. In this case, the hardware processor realizes the functions by reading and executing the program assembled into the circuitry thereof. The hardware processor is not limited to a single circuit, but a plurality of independent circuits may be combined into a single hardware processor to realize the functions. A plurality of constituent elements may be integrated into a single hardware processor to realize the functions.

The constituent elements of the console device 40 or the processing circuitry 50 may be realized by a plurality of pieces of hardware which are distributed. The processing circuitry 50 is not included in the console device 40, but may be realized by a processing device that can communicate with the console device 40. The processing device is, for example, a workstation connected to a single X-ray CT scanner or a device (for example, a cloud server) that is connected to a plurality of X-ray CT scanners and performs the same processing as the processing circuitry 50 which is described below in batch.

The system control function 51 controls various functions of the processing circuitry 50 on the basis of an input operation received by the input interface 43. For example, the system control function 51 sets an energy bin which is referred to by the reconstruction function 53 which will be described later on the basis of the input operation received by the input interface 43. The system control function 51 may automatically set the energy bin regardless of the input operation received by the input interface 43. That is, the energy bin is manually or automatically determined in this embodiment.

The preprocessing function 52 generates projection data from count data by performing predetermined preprocessing on detection data (count data) output from the DAS 16. The predetermined preprocessing may include, for example, a logarithmic transformation process, an offset correction process, an inter-channel sensitivity correction process, a beam hardening correction process, a scattered ray correction process, and a dark count correction process.

The reconstruction function 53 generates a photon counting CT image from the projection data generated by the preprocessing function 52 by performing a predetermined reconstruction process on the projection data. The predetermined reconstruction process may include, for example, a filter-correction reverse projection method or a successive approximation reconstruction method. The reconstruction function 53 stores the reconstructed CT image in the memory 41. When the preprocessing has not been performed by the preprocessing function 52, the reconstruction function 53 may perform a reconstruction process using the detection data (count data).

Figure 3:
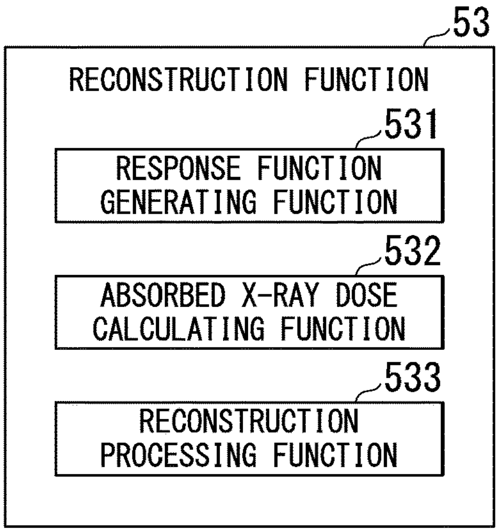
FIG. 3 is a diagram illustrating an example of functional blocks of a reconstruction function according to the embodiment.

FIG. 3 is a diagram illustrating an example of functional blocks of the reconstruction function 53 according to the embodiment. The reconstruction function 53 includes, for example, a response function generating function 531, an absorbed X-ray dose calculating function 532, and a reconstruction processing function 533. The response function generating function 531 generates data of a response function indicating detector response characteristics. For example, the response function generating function 531 measures a response (that is, detection energy and detection intensity) of a standard detection system to a plurality of monochromic X-rays with a plurality of incident X-ray energies by predicting calculation, experiment, and a combination of predicting calculation and experiment and generates a response function on the basis of measured values of the detection energy and the detection intensity. The response function generating function 531 may generate data of a response function on the basis of measured values collected in calibration or the like. The response function defines a relationship between detection energy for each incident X-ray and an output response of a system. For example, the response function defines a relationship between detection energy for each incident X-ray and detection intensity. The generated data of the response function is stored in the memory 41.

The absorbed X-ray dose calculating function 532 calculates an absorbed X-ray dose for each of a plurality of base substances on the basis of count data on a plurality of energy bins included in the projection data, the energy spectrum of X-rays incident on an examinee P, and the response function stored in the memory 41. The absorbed X-ray dose calculating function 532 can calculate an absorbed X-ray dose not affecting the response characteristics of the X-ray detector 15 and the DAS 16 by calculating the absorbed X-ray dose on the basis of the count data and the energy spectrum of X-rays incident on an examinee P using the response function. The process of obtaining an absorbed X-ray dose for each base substance in this way is also referred to as substance discrimination. The type of the base substance can be set to all substances such as calcium, calcification, bone, fat, muscle, air, internal organ, lesion, hard tissue, soft tissue, and contrast medium. The type of the base substance which is a calculation target may be determined by an operator or the like using the input interface 43 in advance. The absorbed X-ray dose indicates an X-ray dose which is absorbed by the base substance. For example, the absorbed X-ray dose is defined by a combination of an X-ray attenuation coefficient and an X-ray transmission path length.

The reconstruction processing function 533 reconstructs a photon counting CT image representing a spatial distribution of a base substance to be imaged out of a plurality of base substances on the basis of the absorbed X-ray dose for each of the plurality of base substances calculated by the absorbed X-ray dose calculating function 532 and stores the generated CT image in the memory 41. The base substance to be imaged may be one type or two or more types. The type of the base substance to be imaged may be determined by an operator or the like using the input interface 43.

The projection data acquired by the photon counting CT scanner includes information of energy of X-rays attenuated by transmitting an examinee P. Accordingly, the reconstruction processing function 533 can reconstruct, for example, a CT image of a specific energy component. The reconstruction processing function 533 can reconstruct, for example, a CT image of each of a plurality of energy components. For example, the reconstruction processing function 533 can allocate color tones corresponding to the energy components to pixels of the CT images of the energy components and overlap the plurality of CT images which are classified according to the energy component.

Description will be continued with reference back to FIG. 1. The image processing function 54 converts the reconstructed CT image to a three-dimensional image or an arbitrary tomographic image using a known method on the basis of the input operation received by the input interface 43.

The scanning control function 55 controls a process of collecting detection data in the frame device 10 by instructing the X-ray high-voltage device 14, the DAS 16, the control device 18, the frame driving device 19, and the bed driving device 32. The scanning control function 55 controls operations of the constituent units when imaging for collecting positioning images and imaging for capturing an image used to diagnosis are performed.

The output control function 56 displays various images (such as a captured image, a positioning image, a GUI image, or a CT image) on the display 42 or transmits various images to an external device (for example, a personal computer used by a doctor) via the communication interface 44.

[Process Flow]

Figure 4:
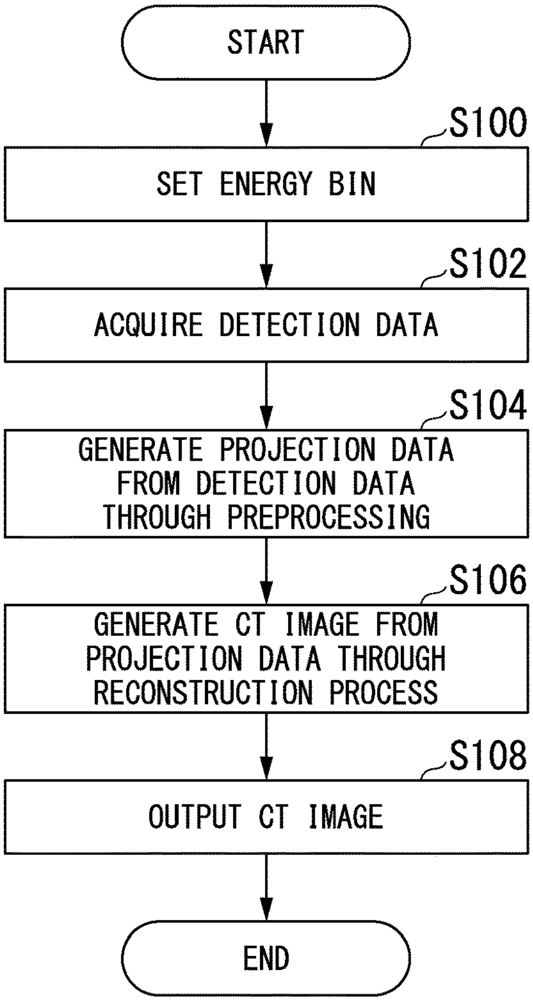
FIG. 4 is a flowchart illustrating a flow of a sequence of processes which is performed by the X-ray CT scanner according to the embodiment.

A flow of a sequence of processes which are performed by the X-ray CT scanner according to the embodiment will be described below. FIG. 4 is a flowchart illustrating a flow of a sequence of processes which are performed by the X-ray CT scanner 1 according to the embodiment. The routine of this flowchart may be performed, for example, when the X-ray CT scanner 1 is calibrated.

First, the system control function 51, for example, sets an energy bin on the basis of an input to the input interface 43 from an operator (Step S100).

Figure 5:
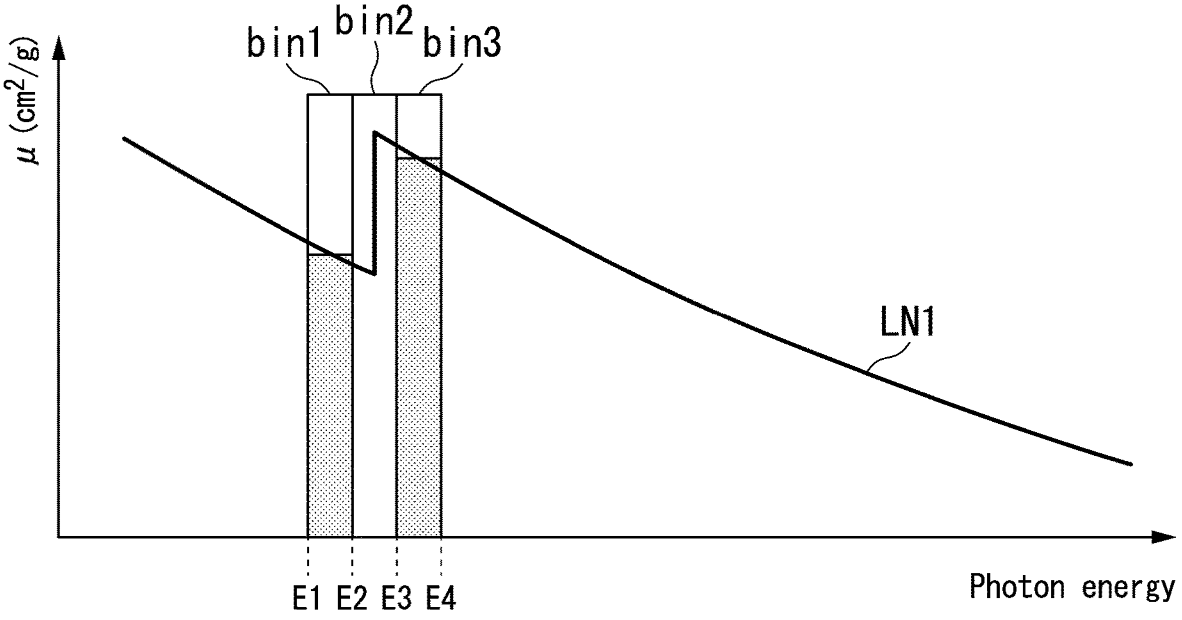
FIG. 5 is a diagram illustrating an example of an energy bin setting method.

FIG. 5 is a diagram illustrating an example of the energy bin setting method. In the drawing, the horizontal axis represents energy of X-ray photons, and the vertical axis represents an X-ray attenuation coefficient. LN1 indicates, for example, energy characteristics of a specific substance such as iodine, gadolinium, or calcium.

For example, the system control function 51 identifies the energy position (a position on the horizontal axis) at which a k-edge (k-absorption edge) occurs in the energy characteristics of the specific substance (on the line LN1). Then, the system control function 51 sets the energy bin bin2 as a non-noticed energy bin in the energy range E2-E3 including the k-edge. The energy range E2-E3 including the k-edge is an example of a "first energy range."

A non-noticed energy bin is the energy bin in which a weighting (also referred to as a weighting coefficient or a contribution factor) for various types of data such as projection data used to reconstruct a CT image is less than that in another energy bin. Typically, the weighting in the non-noticed energy bin is zero. That is, projection data or the like in the non-noticed energy bin is not used to reconstruct a CT image. The non-noticed energy bin is an example of a "first energy bin."

The system control function 51 sets energy bins bin1 and bin2 as noticed energy bins on both sides of (before and after) the energy bin bin2. Specifically, the system control function 51 sets the energy bin bin1 as a noticed energy bin in the energy range E1-E2 with lower energy than the energy range E2-E3 in which the energy bin bin2 is set and sets the energy bin bin3 as a noticed energy bin in the energy range E3-E4 with higher energy than the energy range E2-E3. The energy range E3-E4 is an example of a "second energy range," and the energy range E1-E2 is an example of a "third energy range."

A noticed energy bin is the energy bin in which a weighting (a contribution factor) for various types of data such as projection data used to reconstruct a CT image is greater than a non-noticed energy bin. The energy bin bin3 set as a noticed energy bin in the energy range E3-E4 is an example of a "second energy bin." The energy bin bin1 set as a noticed energy bin in the energy range E1-E2 is an example of a "third energy bin."

Figure 6:
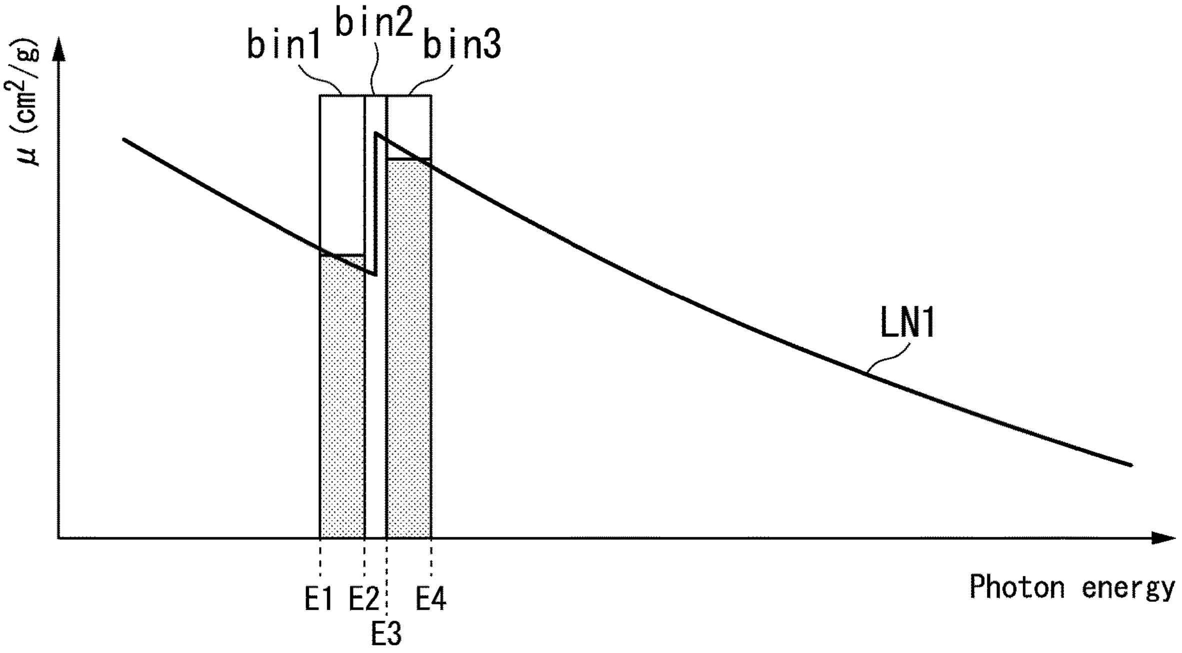
FIG. 6 is a diagram illustrating another example of the energy bin setting method.

FIG. 6 is a diagram illustrating another example of the energy bin setting method. As illustrated in FIG. 6, the system control function 51 may set the width E2-E3 of the energy bin bin2 which is a non-noticed energy bin to be narrower than the width E1-E2 of the energy bin bin1 or the width E3-E4 of the energy bin bin3 which is a noticed energy bin.

For example, the system control function 51 may determine the width of the non-noticed energy bin according to a size of a region of an examinee P irradiated with X-rays. Specifically, the system control function 51 may further narrow the range of the non-noticed energy bin as the size of the region decreases and broaden the range of the non-noticed energy bin as the size of the region increases. Accordingly, it is possible to curb an influence of noise due to the size of an imaging region.

The system control function 51 may determine a width of a non-noticed energy bin according to attributes of an examinee P irradiated with X-rays. Attributes include, for example, age, physical constitution (such as height, weight, and BMI), sex, medical history, and hospitalization days. For example, the system control function 51 may narrow a range of the non-noticed energy bin as a physical constitution of an examinee P decreases and broaden the range of the non-noticed energy bin as the physical constitution increases. Similarly, the system control function 51 may narrow the range of the non-noticed energy bin as the age of an examinee P decreases and broaden the range of the non-noticed energy bin as the age increases. Accordingly, it is possible to curb an influence of noise due to attributes of an examinee P such as physical constitution or age.

The system control function 51 may determine a width of a non-noticed energy bin according to the energy resolution of the X-ray CT scanner 1. For example, the system control function 51 may narrow the range of the non-noticed energy bin as the energy resolution of the X-ray CT scanner 1 increases and broaden the range of the non-noticed energy bin as the energy resolution 1 decreases. Accordingly, it is possible to curb an influence of noise due to the energy resolution of the X-ray CT scanner 1.

Figure 7:
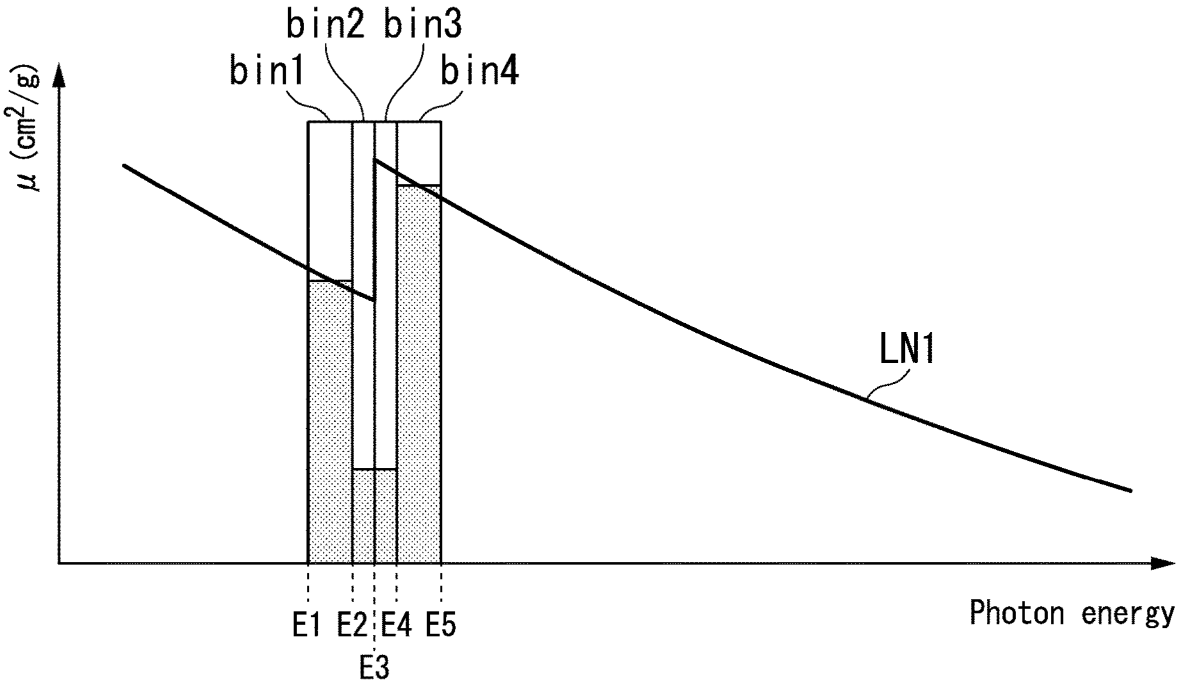
FIG. 7 is a diagram illustrating another example of the energy bin setting method.

FIG. 7 is a diagram illustrating another example of the energy bin setting method. Instead of setting one non-noticed energy bin to include a k-edge as illustrated in FIG. 5 or FIG. 6, the system control function 51 may set two non-noticed energy bins before and after a boundary of the k-edge as illustrated in FIG. 7. Specifically, the system control function 51 may set a first non-noticed energy bin bin2 in the energy range E2-E3 with respect to energy E3 on the boundary of the k-edge and set a second non-noticed energy bin bin3 in the energy range E3-E4. Then, the system control function 51 may set a noticed energy bin bin1 in the energy range E1-E2 before the first non-noticed energy bin bin2 and set a noticed energy bin bin4 in the energy range E4-E5 after the second non-noticed energy bin bin3. At this time, a weighting for the non-noticed energy bins bin2 and bin3 may be a value greater than zero as long as a constraint condition that the weighting is less than a weighting for the noticed energy bins bin1 and bin4 is satisfied. By finely setting the energy bins in the vicinity of the boundary of the k-edge in this way, more data can be used for the reconstruction process and thus it is possible to generate a CT image with higher quality which is robust to noise.

Figure 8:
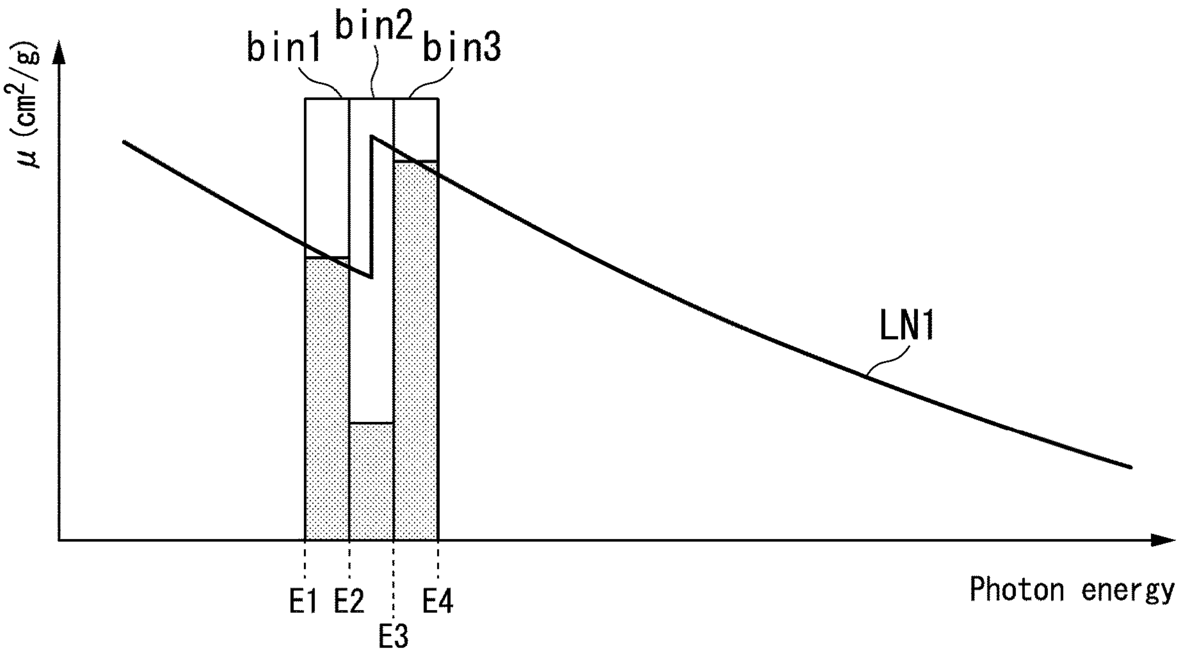
FIG. 8 is a diagram illustrating another example of the energy bin setting method.

FIG. 8 is a diagram illustrating another example of the energy bin setting method. In the example illustrated in FIG. 8, a weighting for a non-noticed energy bin bin2 may be a value greater than zero as long as a constraint condition that the weighting is less than a weighting for noticed energy bins bin1 and bin3 is satisfied similarly to the example illustrated in FIG. 7.

In the aforementioned examples, the weightings for the energy bins are equal to or greater than zero, but the present invention is not limited thereto. For example, the weightings for the energy bins may have minus values. That is, the weightings for the energy bins may have non-positive values.

Figure 9:
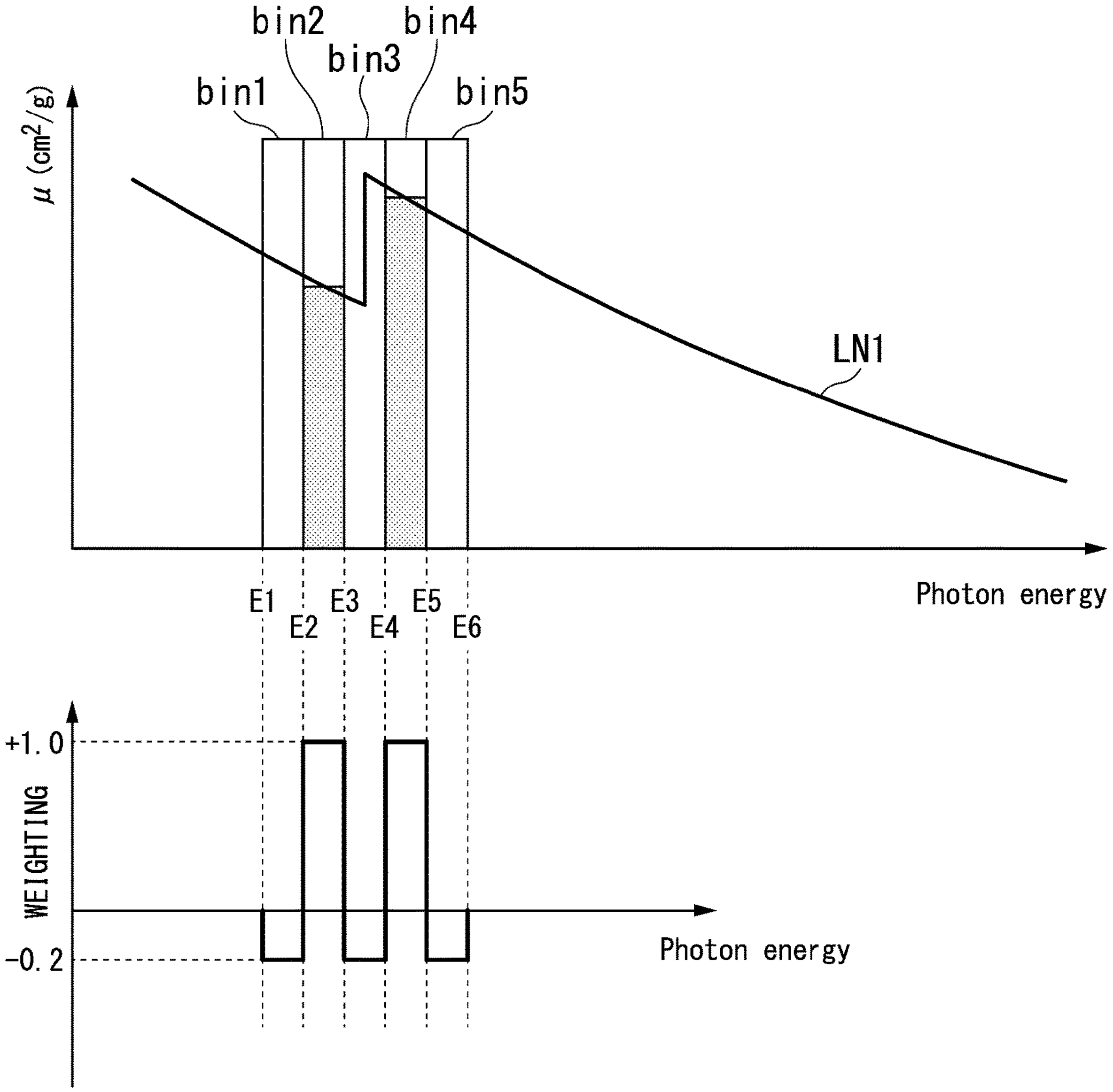
FIG. 9 is a diagram illustrating another example of the energy bin setting method.

FIG. 9 is a diagram illustrating another example of the energy bin setting method. In the example illustrated in FIG. 9, energy bins bin1, bin3, and bin5 are non-noticed energy bins, and energy bins bin2 and bin4 are noticed energy bins. As illustrated in the drawing, for example, weightings for the non-noticed energy bins bin1, bin3, and bin5 may be set to −0.2, and weightings for the noticed energy bins bin2 and bin4 may be set to +1.0. By setting the weightings for the non-noticed energy bins on both sides (before and after) a noticed energy bin to a minus value in this way, it is possible to further emphasize the k-edge.

Figure 10:
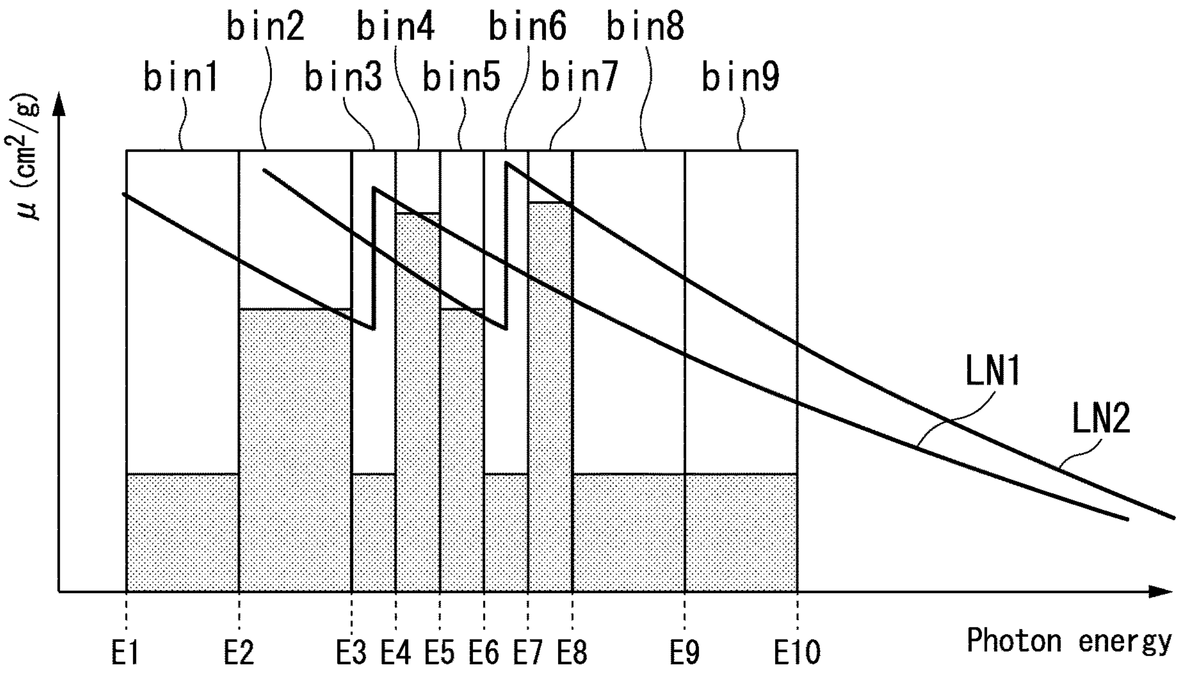
FIG. 10 is a diagram illustrating another example of the energy bin setting method.

FIG. 10 is a diagram illustrating another example of the energy bin setting method. In FIG. 10, LN1 indicates energy characteristics of a first specific substance (for example, iodine), and LN2 indicates energy characteristics of a second specific substance (for example, gadolinium).

When it is intended to detect a plurality of specific substances of different types, the system control function 51 sets non-noticed energy bins in energy ranges including k-edges of the specific substances. In the example illustrated in FIG. 10, the system control function 51 sets the energy bin bin3 as a non-noticed energy bin in the energy range E3-E4 including a k-edge of the first specific substance. Similarly, the system control function 51 sets the energy bin bin6 as a non-noticed energy bin in the energy range E6-E7 including a k-edge of the second specific substance.

The system control function 51 sets noticed energy bins bin1, bin2, bin4, bin5, bin7, bin8, and bin9 in other energy ranges E1-E2, E2-E3, E5-E6, E7-E8, E8-E9 and E9-E10, respectively.

At this time, the system control function 51 may set a width of a noticed energy bin with lower energy than a width of a noticed energy bin with higher energy out of two noticed energy bins set before and after a non-noticed energy bin.

For example, the energy bin bin3 is set as a non-noticed energy bin in the energy range E3-E4 including the k-edge of the first specific substance, the energy bin bin2 is a noticed energy bin before the energy bin bin3, and the energy bin bin4 is a noticed energy bin after the energy bin bin3. In this case, the system control function 51 sets the width of the energy bin bin2 to be greater than the width of the energy bin bin4. In this way, since a tendency that noise is likely to increase as energy becomes lower and noise is likely to decrease as energy increases can be considered, it is possible to generate a CT image with higher quality which is robust to noise.

Description will be continued with reference back to FIG. 4. Then, the DAS 16 collects count data indicating a count number (a counted value) of X-ray photons detected by the X-ray detector 15 for each set energy bin and acquires the count data for each energy bin as detection data (Step S102).

Then, the preprocessing function 52 performs preprocessing on the detection data (count data) acquired by the DAS 16 and generates projection data for each energy bin (Step S104). The projection data is an example of "data based on X-ray photons."

Then, the reconstruction function 53 performs the reconstruction process on the projection data generated by the preprocessing function 52 and generates a CT image from the projection data (Step S106).

For example, the reconstruction function 53 may generate a CT image (a spectral image) including only the specific substance by extracting only a component of a specific substance (for example, iodine) from the projection data for each energy bin and reconstructing the projection data for each energy bin from which the component of the specific substance has been extracted.

The reconstruction function 53 may generate a CT image (a normal CT image) including various substances by weighting the projection data for each energy bin using an average energy value of the energy bins, adding the weighted data, and reconstructing the weighted and added data. Instead, the reconstruction function 53 may sum the projection data for each energy bin, calculate an absorbed X-ray dose on the basis of the total sum of the projection data and a response function stored in the memory 41, and generate a normal CT image on the basis of the absorbed X-ray dose. The normal CT image is an example of a "first medical image."

The reconstruction function 53 may generate a CT image (a k-edge emphasized image which is a kind of spectral image) in which a specific substance is further emphasized in comparison with the normal CT image by reconstructing the projection data for each noticed energy bins before and after the non-noticed energy bin and may generate a difference image between the normal CT image and the k-edge emphasized image. In the example illustrated in FIG. 10, the reconstruction function 53 generates a k-edge emphasized image in which the first spectral image (for example, iodine) is emphasized by reconstructing the projection data for the noticed energy bins bin2 and bin4 before and after the non-noticed energy bin bin3. Similarly, the reconstruction function 53 generates a k-edge emphasized image in which the second spectral image (for example, gadolinium) is emphasized by reconstructing the projection data for the noticed energy bins bin5 and bin7 before and after the non-noticed energy bin bin6. The k-edge emphasized image is an example of a "second medical image."

The reconstruction function 53 sets the weighting for the projection data in a non-noticed energy bin for generating a k-edge emphasized image to be less than the weighting for the projection data in a noticed energy bin for generating the k-edge emphasized image.

In the example illustrated in FIG. 10, when the k-edge emphasized image in which the first specific substance (for example, iodine) is emphasized is generated, the reconstruction function 53 sets the weighting for the projection data in the non-noticed energy bin bin3 to be less than the weighting for the projection data in the noticed energy bins bin2 and bin4. Similarly, when the k-edge emphasized image in which the second specific substance (for example, gadolinium) is emphasized is generated, the reconstruction function 53 sets the weighting for the projection data in the non-noticed energy bin bin6 to be less than the weighting for the projection data in the noticed energy bins bin5 and bin7.

The reconstruction function 53 sets the weighting for the projection data in a non-noticed energy bin for generating a k-edge emphasized image to be less than the weighting for the projection data in a non-noticed energy bin for generating a normal CT image.

In the example illustrated in FIG. 10, the reconstruction function 53 sets the weighting for the projection data in the non-noticed energy bin bin3 used to generate the k-edge emphasized image in which the first specific substance (for example, iodine) is emphasized to be less than the weighting for the projection data in the non-noticed energy bin bin3 used to generate the normal CT image. Similarly, the reconstruction function 53 sets the weighting for the projection data in the non-noticed energy bin bin6 used to generate the k-edge emphasized image in which the second specific substance (for example, gadolinium) is emphasized to be less than the weighting for the projection data in the non-noticed energy bin bin6 used to generate the normal CT image.

Then, the output control function 56 displays various reconstructed CT images (the normal CT image, the spectral image, and the difference image) on the display 42 or transmits the CT images to an external device via the communication interface 44 (Step S108). Then, the routine of the flowchart ends.

According to the aforementioned embodiment, the processing circuitry 50 of the X-ray CT scanner 1 sets a non-noticed energy bin in the energy range including a k-edge (k-absorption edge) of a specific substance such as iodine, gadolinium, or calcium and sets noticed energy bins in energy ranges (a range with higher energy and a range with lower energy) on both sides of the energy range including the k-edge energy. The processing circuitry 50 performs preprocessing on count data indicating the number of X-ray photons counted for each energy bin and generates projection data for each energy bin. The processing circuitry 50 performs a reconstruction process on the projection data for each energy bin and generates a CT image.

For example, the processing circuitry 50 generates a CT image including various substances (that is, a normal CT image) by summing and reconstructing the projection data in all the energy bins including the non-noticed energy bins and the noticed energy bins and generates a CT image in which a specific substance is further emphasized (that is, a k-edge emphasized image) in comparison with the normal CT image by reconstructing the projection data in the noticed energy bins before and after the non-noticed energy bin.

At this time, the processing circuitry 50 sets the weighting for the projection data in the non-noticed energy bin when the k-edge emphasized image is generated to be less than the weighting for the projection data in the noticed energy bins when the k-edge emphasized image is generated. The processing circuitry 50 sets the weighting for the projection data in the non-noticed energy bin when the k-edge emphasized image is generated to be less than the weighting for the projection data in the non-noticed energy bin when the normal CT image is generated.

The processing circuitry 50 may generate a difference image between the normal CT image and the spectral image.

Then, the processing circuitry 50 displays the normal CT image, the spectral image, and the difference image on the display 42 or transmits the images to an external device via the communication interface 44.

In this way, it is possible to generate a CT image with higher quality by setting a non-noticed energy bin to include k-edge energy, setting noticed energy bins before and after the non-noticed energy bin, and weighting and reconstructing projection data for each energy bin.

OTHER EMBODIMENTS

Other embodiments will be described below. In the aforementioned embodiment, the processing circuitry 50 of the console device 40 of the X-ray CT scanner 1 generates a CT image with higher quality by setting a non-noticed energy bin and noticed energy bins and weighting the projection data or the energy image for each energy bin, but the present invention is not limited thereto. For example, an external medical information processing device such as a workstation or a server may perform such various processes. That is, some or all functions of the processing circuitry 50 of the console device 40 may be taken charge of by an external medical information processing device.

In the aforementioned embodiment, the reconstruction function 53 of the processing circuitry 50 adjusts the weights for the projection data in the energy bins, but the present invention is not limited thereto. For example, the reconstruction function 53 may generate a first spectral image by performing the reconstruction process on the projection data in a non-noticed energy bin, generate a second spectral image by performing the reconstruction process on the projection data in noticed energy bins, and generate a normal CT image or a k-edge emphasized image by adjusting weightings for the first and second spectral images and synthesizing the first and second spectral images. At this time, typically, the weighting for the first spectral image derived from the projection data in the non-noticed energy bin may be zero. The spectral image is another example of the "data based on X-ray photons."

In the aforementioned embodiment, the output control function 56 of the processing circuitry 50 may simultaneously display the normal CT image and the k-edge emphasized image on the display 42 such that they overlap each other. At this time, the output control function 56 may display only the k-edge emphasized image in a region of interest (ROI) designated by a user and display the normal CT image in the other region.

Figure 11:
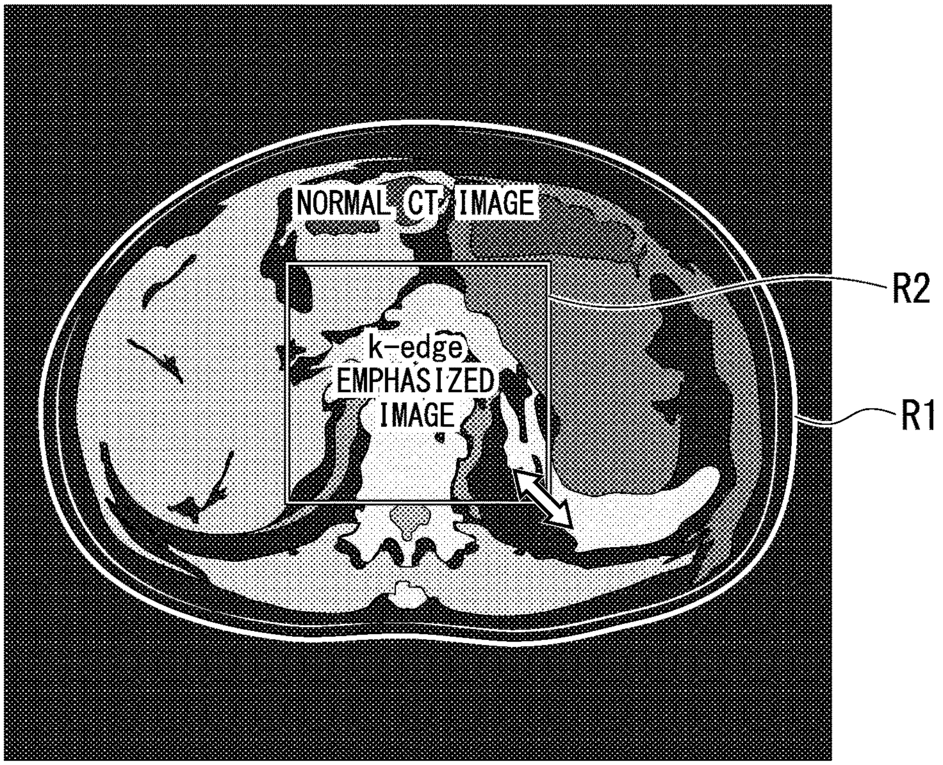
FIG. 11 is a diagram illustrating an example of a screen of a display.

FIG. 11 is a diagram illustrating an example of a screen of the display 42. In the example illustrated in the drawing, a sectional image of a trunk of an examinee P is illustrated. R1 indicates the whole region of a trunk section, and R2 indicates a region of interest (a partial region of R1) designated by a user. For example, the user may set one or more regions of interest R2 using the input interface 43. When at least one region of interest R is set by the user, the output control function 56 of the processing circuitry 50 may display a k-edge emphasized image in the region of interest R2 and display a normal CT image in the whole region R1 other than the region of interest R2.

While some embodiments have been described above, the embodiments are presented as only an example and are not intended to limit the scope of the invention. The embodiments can be modified in various other forms and various omissions, substitutions, and alterations can be performed thereto without departing from the gist of the invention. These embodiments or modifications thereof are included in the scope or gist of the invention and are included in the inventions described in the appended claims and scopes equivalent thereto.

What is claimed is:

1. A medical image processing device, comprising:

processing circuitry configured to perform:

setting a first energy bin in a first energy range including energy of a k-absorption edge of a specific substance;

setting a second energy bin in a second energy range with higher energy than the first energy range;

setting a third energy bin in a third energy range with lower energy than the first energy range;

generating a first medical image and a second medical image in which the specific substance is more emphasized in comparison with the first medical image using data based on X-ray photons counted in each of the first energy bin, the second energy bin, and the third energy bin; and outputting the first medical image and the second medical image via an output interface, wherein the processing circuitry sets a weighting for the data in the first energy bin when the second medical image is generated to be less than a weighting for the data in the second energy bin when the second medical image is generated and to be less than a weighting for the data in the first energy bin when the first medical image is generated, wherein the processing circuitry sets the weighting for the data in the first energy bin when the second medical image is generated to be less than a weighting for the data in the third energy bin when the second medical image is generated and to be less than the weighting for the data in the first energy bin when the first medical image is generated, and wherein the processing circuitry generates the second medical image by reconstructing the weighted data in the first energy bin, the weighted data in the second energy bin, and the weighted data in the third energy bin.

2. The medical image processing device according to claim 1, wherein the processing circuitry sets the weighting for the data in the first energy bin when the second medical image is generated to zero or a minus value or does not use the data in the first energy bin when the second medical image is generated.

3. The medical image processing device according to claim 1, wherein the processing circuitry performs preprocessing on count data indicating a number of X-ray photons counted for each energy bin and generates projection data from the count data, and wherein the processing circuitry adjusts the weighting for the projection data.

4. The medical image processing device according to claim 1, wherein the processing circuitry performs preprocessing on count data indicating a number of X-ray photons counted for each energy bin and generates projection data from the count data, wherein the processing circuitry performs a reconstruction process on the projection data in the first energy bin and generates a first spectral image, wherein the processing circuitry performs the reconstruction process on the projection data in the second energy bin and generates a second spectral image, wherein the processing circuitry performs the reconstruction process on the projection data in the third energy bin and generates a third spectral image, wherein the processing circuitry generates the first medical image and the second medical image by combining the first spectral image, the second spectral image, and the third spectral image, and wherein the processing circuitry adjusts the weighting for each of the first spectral image, the second spectral image, and the third spectral image.

5. The medical image processing device according to claim 4, wherein the processing circuitry sets the weighting for the first spectral image when the second medical image is generated to zero or a minus value.

6. The medical image processing device according to claim 1, wherein the processing circuitry determines a range of the first energy bin based on a size of a region of an examinee irradiated with X-rays.

7. The medical image processing device according to claim 6, wherein the processing circuitry narrows the range of the first energy bin as the size of the region decreases and broadens the range of the first energy bin as the size of the region increases.

8. The medical image processing device according to claim 1, wherein the processing circuitry determines a range of the first energy bin based on attributes of an examinee irradiated with X-rays.

9. The medical image processing device according to claim 8, wherein the attributes include a physical constitution of the examinee, and wherein the processing circuitry narrows the range of the first energy bin as the physical constitution decreases and broadens the range of the first energy bin as the physical constitution increases.

10. The medical image processing device according to claim 8, wherein the attributes include an age of the examinee, and wherein the processing circuitry narrows the range of the first energy bin as the age decreases and broadens the range of the first energy bin as the age increases.

11. The medical image processing device according to claim 1, wherein the processing circuitry determines a range of the first energy bin based on an energy resolution of an X-ray CT scanner irradiating an examinee with X-rays.

12. The medical image processing device according to claim 11, wherein the processing circuitry narrows the range of the first energy bin as the energy resolution increases and broadens the range of the first energy bin as the energy resolution decreases.

13. The medical image processing device according to claim 1, wherein the processing circuitry sets a width of the third energy bin set in the third energy range to be greater than a width of the second energy bin set in the second energy range.

14. The medical image processing device according to claim 1, wherein the processing circuitry generates a difference image between the first medical image and the second medical image, and wherein the processing circuitry outputs the difference image via the output interface.

15. The medical image processing device according to claim 1, wherein the output interface includes a display, wherein the medical image processing device further comprises an input interface which is able to be operated by a user, and wherein the processing circuitry displays the second medical image in a region of interest, which is a region designated by the user on a screen of the display, and displays the first medical image in a region other than the region of interest when a region in which the second medical image is displayed is designated by the user using the input interface.

16. A medical image processing method that is performed by a computer, the medical image processing method comprising:

setting a first energy bin in a first energy range including energy of a k-absorption edge of a specific substance;

setting a second energy bin in a second energy range with higher energy than the first energy range;

setting a third energy bin in a third energy range with lower energy than the first energy range;

generating a first medical image and a second medical image in which the specific substance is more emphasized in comparison with the first medical image using data based on X-ray photons counted in each of the first energy bin, the second energy bin, and the third energy bin;

outputting the first medical image and the second medical image via an output interface;

setting a weighting for the data in the first energy bin when the second medical image is generated to be less than a weighting for the data in the second energy bin when the second medical image is generated and to be less than a weighting for the data in the first energy bin when the first medical image is generated;

setting the weighting for the data in the first energy bin when the second medical image is generated to be less than a weighting for the data in the third energy bin when the second medical image is generated and to be less than the weighting for the data in the first energy bin when the first medical image is generated; and generating the second medical image by reconstructing the weighted data in the first energy bin, the weighted data in the second energy bin, and the weighted data in the third energy bin.

* * * * *